(12) United States Patent
Sode et al.

(10) Patent No.: US 8,492,084 B2
(45) Date of Patent: Jul. 23, 2013

(54) METHOD AND APPARATUS FOR ASSAYING TEST SUBSTANCE IN SAMPLE

(76) Inventors: Koji Sode, Fuchu (JP); Kazunori Ikebukuro, Fuchu (JP); Hiroki Yamazaki, Yokohama (JP)

( * ) Notice: Subject to any disclaimer, the term of this patent is extended or adjusted under 35 U.S.C. 154(b) by 370 days.

(21) Appl. No.: 12/162,008

(22) PCT Filed: Jan. 24, 2007

(86) PCT No.: PCT/JP2007/051050
§ 371 (c)(1),
(2), (4) Date: Oct. 2, 2008

(87) PCT Pub. No.: WO2007/086403
PCT Pub. Date: Aug. 2, 2007

(65) Prior Publication Data
US 2009/0305254 A1    Dec. 10, 2009

(30) Foreign Application Priority Data

Jan. 24, 2006  (JP) .................................. 2006-014624
Sep. 27, 2006  (JP) .................................. 2006-261801

(51) Int. Cl.
*C12Q 1/68*   (2006.01)

(52) U.S. Cl.
USPC ........................................................ 435/6.1

(58) Field of Classification Search
USPC ........................................................ 435/6.1
See application file for complete search history.

(56) References Cited

U.S. PATENT DOCUMENTS

| | | | |
|---|---|---|---|
| 8,143,004 B2 * | 3/2012 | Ikebukuro et al. | 435/6.11 |
| 2002/0197614 A1 | 12/2002 | Weir et al. | |
| 2005/0078179 A1 | 4/2005 | Hamada et al. | |
| 2005/0089864 A1 * | 4/2005 | Li et al. | 435/6 |
| 2005/0233317 A1 | 10/2005 | Kumar et al. | |
| 2006/0068407 A1 * | 3/2006 | Rupcich et al. | 435/6 |
| 2007/0154909 A1 * | 7/2007 | Xiao et al. | 435/6 |
| 2008/0051339 A1 * | 2/2008 | Sullenger et al. | 514/12 |

FOREIGN PATENT DOCUMENTS

| | | |
|---|---|---|
| EP | 1219708 A1 | 7/2002 |
| WO | 00/60118 A2 | 10/2000 |
| WO | 01/27263 A1 | 4/2001 |
| WO | WO 2005049826 A1 * | 6/2005 |

OTHER PUBLICATIONS

Tyagi et al. (1996) Nat. Biotechnology 14:303-308.*
Steemers et al. (2000) Nature Biotechnology vol. 18: 91-94.*
Nutiu et al. (2005) "In vitro selection of structure-switching signaling aptamers" Agnew Chem Int. Ed. 44:1061-1065.*
Ikebukuro et al. "Development of aptamer based protein detection system using DNA immobilized support for bound/free separation", The Electrochemical Society of Japan, Apr. 1, 2006, p. 231, 3J07.*
Ikebukuoro et al. (2004) Nucleic Acids Symposium Series No. 48: 231-232.*
Igarashi et al. (2004) Archives of Biochemistry and Biophysics 428: 52-63.*
Ikebukuro et al. (2005) "Novel Electronic Sensor System for Prorteins Using the aptamers in Sandwich Manner," Biosens. Bioelectron. 20(10):2168-2172.
International Search Report PCT/JP2007/051050 (Mar. 2007).

* cited by examiner

*Primary Examiner* — Brian Whiteman
(74) *Attorney, Agent, or Firm* — Edell, Shapiro & Finnan, LLC (57) ABSTRACT

Disclosed are a method for assaying a target substance in a sample and an apparatus for the method. The method can specifically assay the target substance in the sample without using any antibody against the target substance. The assaying method includes simultaneously or successively bringing a labeled aptamer, the target substance in the sample and a solid phase into contact together, and then measuring the label of the aptamer which has not been bound on the solid phase. The labeled aptamer has a property of binding to the target substance. The solid phase carries an oligonucleotide immobilized on it in an excess amount relative to the target substance. The oligonucleotide is hybridizable with the labeled aptamer when the labeled aptamer is in a state that it is not bound to the target substance, but is not hybridizable with the labeled aptamer when the labeled aptamer is in a state that it is bound to the target substance.

19 Claims, 6 Drawing Sheets

SEQUENCE LISTING

```
<160> NUMBER OF SEQ ID NOS: 8

<210> SEQ ID NO 1
<211> LENGTH: 15
<212> TYPE: DNA
<213> ORGANISM: Artificial Sequence
<220> FEATURE:
<223> OTHER INFORMATION: single-stranded region in aptamer

<400> SEQUENCE: 1
acgaattcat gatca                                                      15

<210> SEQ ID NO 2
<211> LENGTH: 25
<212> TYPE: DNA
<213> ORGANISM: Artificial Sequence
<220> FEATURE:
<223> OTHER INFORMATION: hairpin structure in aptamer

<400> SEQUENCE: 2
ggacgacgaa ttcatgatca cgtcc                                           25

<210> SEQ ID NO 3
<211> LENGTH: 33
<212> TYPE: DNA
<213> ORGANISM: Artificial Sequence
<220> FEATURE:
<223> OTHER INFORMATION: single-stranded region in aptamer of Example 1

<400> SEQUENCE: 3
cactggtagg ttggtgtggt tttggggcca gtg                                  33

<210> SEQ ID NO 4
<211> LENGTH: 58
<212> TYPE: DNA
<213> ORGANISM: Artificial Sequence
<220> FEATURE:
<223> OTHER INFORMATION: structure-switching aptamer of Example 1
```

-continued

```
<400> SEQUENCE: 4
cactggtagg ttggtgtggt tggacgacga attcatgatc acgtccttgg ggccagtg        58

<210> SEQ ID NO 5
<211> LENGTH: 31
<212> TYPE: DNA
<213> ORGANISM: Artificial Sequence
<220> FEATURE:
<223> OTHER INFORMATION: CaAp-1 aptamer of Example 2

<400> SEQUENCE: 5
tcacgtttat ccgtccctcc tagtggcgtg a                                     31

<210> SEQ ID NO 6
<211> LENGTH: 14
<212> TYPE: DNA
<213> ORGANISM: Artificial Sequence
<220> FEATURE:
<223> OTHER INFORMATION: immobilized oligonucleotide (14-mer capture
      oligonucleotide)

<400> SEQUENCE: 6
acggataaac gtga                                                        14

<210> SEQ ID NO 7
<211> LENGTH: 27
<212> TYPE: DNA
<213> ORGANISM: Artificial Sequence
<220> FEATURE:
<223> OTHER INFORMATION: hairpin structure of Figure 1

<400> SEQUENCE: 7
tggacgacga attcatgatc acgtcct                                          27

<210> SEQ ID NO 8
<211> LENGTH: 15
<212> TYPE: DNA
<213> ORGANISM: Artificial Sequence
<220> FEATURE:
<223> OTHER INFORMATION: oligonucleotide (15-mer complementary strand)

<400> SEQUENCE: 8
tgatcatgaa ttcgt                                                       15
```

METHOD AND APPARATUS FOR ASSAYING TEST SUBSTANCE IN SAMPLE

CROSS-REFERENCE TO RELATED APPLICATIONS

This application is a 35 U.S.C. §371 National Stage Application of United States Patent Application Serial No. PCT/JP2007/051050 (pending; filed Jan. 24, 2007), which application is herein incorporated by reference in its entirety.

TECHNICAL FIELD

This invention relates to a method for assaying a target substance in a sample and an apparatus therefor.

BACKGROUND ART

Assay of a protein or the like in a sample is primarily performed by immunoassay these days. As immunoassay, a variety of methods are known and have been put to practical use. Whichever method is chosen, a specific antibody against a target substance is used. Creation of a specific antibody against a target substance can be conducted by a method known per se in the art, but is laborious so that the specific antibody is costly.

On the other hand, there are also known aptamers which are nucleic acid molecules that specifically bind to desired molecules. An aptamer that specifically binds to a desired target molecule can be created by a method called "SELEX (Systematic Evolution of Ligands by EXponential Enrichment)" (Non-patent Document 1). According to this method, the target molecule is immobilized on a carrier, to which a nucleic acid library including a huge variety of nucleic acids having random base sequences is added. One of the nucleic acids, which has bound to the target molecule, is collected, amplified by PCR, and is again added to the carrier with the target molecule immobilized thereon. By repeating this step 10 times or so, the aptamer having high binding ability to the target molecule is concentrated. Its base sequence is then determined to acquire the aptamer that recognizes the target molecule. It is to be noted that the above-described nucleic acid library can be readily prepared by binding nucleotides at random in an automated chemical synthesizer for nucleic acids. By the method that makes use of a nucleic acid library having random base sequences and makes positive use of accidents as described above, it is possible to create an aptamer that specifically binds to a desired target substance. Further, an aptamer generally has a single-stranded region. It is also known to create, by a modified SELEX method, an aptamer called "structure-switching aptamer" that an oligonucleotide complementary to the single-stranded region is hybridizable with the single-stranded region when the aptamer is in a state that it is not bound to a target substance but is not hybridizable with the single-stranded region when the aptamer is in a state that it is bound to the target substance (Non-patent Document 2).

Patent Document 1: Japanese Patent Laid-open No. 2003-294679
Patent Document 2: Japanese Patent Laid-open No. 2003-294680
Patent Document 3: Japanese Patent Laid-open No. 2003-294681
Non-patent Document 1: Tuerk, C. and Gold, L., Science, 294, 505-510 (1990)
Non-patent Document 2: Angew. Chem. Int. Ed., 44, 1061-1065 (2005)
Non-patent Document 3: Kazunori Ikebukuro, et al., Nucleic Acids Research, 33(12), e108
Non-patent Document 4: Wiegand T. W., Williams P. B., Dreskin S. C., Jouvin M. H., Kinet J. P., Tasset D., High-affinity oligonucleotide ligands to human IgE inhibit binding to Fc epsilon receptor I, JOURNAL OF IMMUNOLOGY, 157(1), 221-230 (JUL 1, 1996)

DISCLOSURE OF THE INVENTION

The Problem to be Solved by the Invention

Objects of the present invention are to provide a method of assaying a target substance, which can specifically assay the target substance in a sample without using any antibody against the target substance, and also an apparatus for the method.

Means for Solving the Problem

As a result of enthusiastic research, the present inventors found that a target substance in a sample can be assayed by providing a labeled aptamer, with which an oligonucleotide is hybridizable in a state that the labeled aptamer is not bound to the target substance but is not hybridizable when the labeled aptamer is in a state that it is bound to the target substance; bringing the aptamer into contact with the sample; bringing the aptamer, to which the target substance has not bound, into contact with the oligonucleotide, which is immobilized and is hybridizable with the aptamer, to bind the aptamer on the solid phase; and measuring the label of the aptamer which has not be bound to the solid phase. The finding has lead to the completion of the present invention.

Described specifically, the present invention provides a method for assaying a target substance in a sample, including simultaneously or successively bringing a labeled aptamer, which has a property of binding to the target substance and with which an oligonucleotide is hybridizable when the labeled aptamer is in a state that it is not bound to the target substance but is not hybridizable when the labeled aptamer is in a state that it is bound to the target substance, the target substance in the sample, and a solid phase, on which the oligonucleotide has been immobilized in an excess amount relative to the target substance, into contact together; and then measuring the label of the aptamer which has not been bound on the solid phase. Further, the present invention also provides a solid phase useful in the above-described method according to the present invention, including a carrier and the oligonucleotide immobilized thereon. Furthermore, the present invention also provides an assaying apparatus for a target substance in a sample, including the above-described solid phase according to the present invention and a capture region for capturing the aptamer subsequent to its contact with the solid phase.

Advantageous Effects

By the present invention, there have been provided a novel assaying method capable of specifically assaying a target substance without using any antibody against the target substance and also a solid phase and apparatus for the method. An aptamer can be prepared by using an automated chemical synthesizer, and therefore, can be prepared far more easily and economically compared with a specific antibody. Owing to this, the present invention has made it possible to perform the specific assay of various target substances at ever lower cost. Therefore, the present invention is believed to substantially contribute to diverse fields such as the diagnosis of various diseases, the quality inspection of food and drink, and the measurement of contamination degrees by noxious substances in environments.

BEST MODES FOR CARRYING OUT THE INVENTION

No limitation is imposed at all on the target substance to be measured by the method of the present invention insofar as it is possible to prepare an aptamer that specifically binds to the target substance. Illustrative can be various proteins (including protein conjugates such as glycoproteins and lipoproteins), saccharides (including saccharide conjugates such as polysaccharides, oligosaccharides, monosaccharides and glycolipids), lipids, nucleic acids, and lower-molecular compounds. An aptamer is created by a method making positive use of accidents like SELEX as mentioned above, so that for substantially all target molecules, it is possible to create aptamers that specifically bind to them. Thrombin was assayed as a target substance in Example 1 to be described subsequently herein, while immunoglobulin (IgE) was assayed as a target substance in Example 2 to be described subsequently herein. As described above, however, target substances are not limited to them, and preferred specific examples can include insulin and glucagons useful as marker molecules for diseases, α-fetoprotein useful as a hepatic cancer marker, CEA as a digestive cancer marker, PSA as a prostate cancer marker, CA125 as an ovarian cancer marker, CA19-9 as a pancreatic cancer marker, and HIV virus antibody, hepatitis virus C antibody, hepatitis virus A antibody and hepatitis virus B antibody useful as markers for various infectious diseases. It is to be noted that the term "assay" as used herein encompasses therein quantitation, semiquantitation, and detection.

The aptamer for use in the present invention is a labeled aptamer, which has a property of binding to a target substance and with which an oligonucleotide is hybridizable when the labeled aptamer is in a state that it is not bound to the target substance but is not hybridizable when the labeled aptamer is in a state that it is bound to the target substance. No particular limitation is imposed on the size of the aptamer to be used in the present invention. In general, however, its size may be 30-mers to 100-mers or so, with 50-mers to 70-mers or so being preferred ("mer" indicates the number of nucleotides). Further, the aptamer can be either DNA or RNA, or another artificial nucleic acid, although DNA is preferred for its chemical stability and the readiness of its automated chemical synthesis.

The aptamer may preferably have a looped, single-stranded region, and preferably, regions adjacent the opposite ends of the single-stranded region may mutually form a double-stranded region. No particular limitation is imposed on the size of the single-stranded region, but 8-mers to 25-mers are preferred. On the other hand, the sizes of the regions which are adjacent the opposite ends of the single-stranded region and mutually form the double-stranded region (which may hereinafter be called "adjacent double-strand forming regions") may preferably be, but are not specifically limited to, 2 bp to 10 bp.

The aptamer for use in the present invention has been labeled. As labels, known labels commonly employed in immunoassay can be adopted. For example, enzyme labels, fluorescent labels, radiolabels, gold colloid labels and the like can be adopted. Among these, enzymes which catalyze electrochemically-measurable reactions are preferred, because they permit an electrochemical measurement, a measuring system is simple and permits easy miniaturization, integration and mass production, and an automated apparatus can be readily designed. Examples of these enzymes include, but are not limited to, glucose dehydrogenase, glucose oxidase, β-galactosidase, and the like. It is to be noted that a labeled enzyme is not necessarily limited to an enzyme which catalyzes an electrochemically-measurable reaction but alkaline phosphatase, horseradish peroxidase or the like, which is commonly employed, for example, in enzyme immunoassay (ELISA) and the like to catalyze a staining reaction, can be also adopted. Such a label may be caused to bind to an aptamer subsequent to the preparation of the aptamer by a method known per se in the art. As an alternative, a labeled aptamer can also be obtained by using a primer, which contains a label bound to an end thereof (an end on the side that the end becomes the end of an amplified polynucleotide), as a primer for PCR to be conducted in the course of the below-mentioned preparation of the aptamer by SELEX.

No particular limitation is imposed on the immobilized oligonucleotide to be hybridized with the aptamer insofar as the oligonucleotide can bind the aptamer on the solid phase by its hybridization with the aptamer under a measuring condition described later. Preferably, however, the oligonucleotide may contain a region, which is complementary to at least a continuous part in the aptamer and has a size of from 4-mers to 25-mers, with 8-mers to 25-mers being more preferred. It is particularly preferred that the aptamer is equipped with the above-described looped, single-stranded region and that the immobilized oligonucleotide contains a region which is complementary to at least a continuous part in the single-stranded region and has a size of from 4-mers to 25-mers, more preferably from 8-mers to 25-mers. Still more preferably, the immobilized oligonucleotide may be a complementary strand to the single-stranded region and may have the same size as the single-stranded region. It is, however, to be noted that the immobilized oligonucleotide is not necessarily limited to one hybridizable only with the single-stranded region of the aptamer but that insofar as its part is hybridizable with the single-stranded region, it can cut into and hybridize with the double-stranded region of the aptamer. In other words, the immobilized oligonucleotide may also be one hybridizable with a region that extends over the single-stranded region and the double-stranded region of the aptamer. In this case, the immobilized oligonucleotide may preferably be such an immobilized oligonucleotide that 25% or more, more preferably 45% or more of its size hybridizes with the single-stranded region, and in particular, the immobilized oligonucleotide may preferably be a complementary strand to the region of the aptamer. In Example 1 to be described subsequently herein, the single-stranded region has the base sequence of acgaattcatgatca (SEQ ID NO: 1), and the single-stranded region and adjacent double-strand forming regions have the base sequence of ggacgacgaattcatgatcacgtcc (SEQ ID NO: 2). As is evident from a comparison between SEQ ID NO: 1 and SEQ ID NO: 2, the 5-base parts at the opposite ends of SEQ ID NO: 2 are the adjacent double-strand forming regions, and these adjacent double-strand forming regions are paired each other to form the double-stranded region. It is, however, to be noted that the base sequences of the single-stranded region and adjacent double-strand forming region are not limited to the base sequence represented by SEQ ID NO: 2 and can be set as desired by a method to be described subsequently herein. On the other hand, the hairpin structure having the base sequence represented by SEQ ID NO: 2 can be used in the thrombin-specific aptamer to be described in Example 1 and further, can be included in an aptamer that specifically binds to a desired target substance. It is to be noted that the expression "having a base sequence" as used herein means that the bases of a nucleic acid are arrayed in such an order. For example, the expression "single-stranded region having a base sequence represented by acgaattcatgatca," (SEQ ID NO: 1) therefore, means a single-stranded region of 15-base size having the base sequence of acgaattcatgatca (SEQ ID NO: 1).

The above-described oligonucleotide is used subsequent to its immobilization on a solid phase. In other words, the oligonucleotide is used in a state that it is bound on a solid carrier. For the immobilization of an oligonucleotide on a solid phase, methods themselves are well known. For example, by covalently binding biotin to one end of an oligonucleotide and further, immobilizing avidin on a carrier beforehand, the oligonucleotide can be bound to the carrier via an avidin-biotin bond. However, the immobilization method is not limited to the above-described method, and an oligonucleotide may be caused to covalently and directly bind to a carrier by glutaraldehyde crosslinking or the like. An oligonucleotide may also be physically adsorbed on a film or the like, which is made of nylon, nitrocellulose or the like that adsorbs DNA well. Further, an oligonucleotide can bind to a carrier directly or can bind to a carrier via a low-molecular compound such as biotin. Moreover, an oligonucleotide can also bind to a carrier via a spacer. For example, a longer oligonucleotide which contains at one end thereof an oligonucleotide to be immobilized is prepared, and the oligonucleotide can then be caused to bind at the opposite end thereof to a carrier via the above-described biotin-avidin bond. In the nucleic acid immobilized on the carrier in the above case, the polynucleotide segments other than the oligonucleotide to be immobilized function as mere spacers so that no limitation is imposed on their base sequences or sizes. As the carrier to be used as the solid phase, one commonly employed for the immobilization of nucleic acids can be used as it is. For example, avidin beads with avidin immobilized on beads made of a synthetic resin or a high-molecular substance such as agarose are commercially available, and therefore, their commercial product can be used as it is. As an alternative, a commercially-available base plate for DNA chip, said substrate being made of glass, silicon or a synthetic resin, can also be used. As such a carrier, a column-shaped carrier such as that used in chromatography or a filter-shaped carrier can also be adopted in place of a beads-shaped or plate-shaped carrier.

An aptamer for use in the present invention is hybridizable with an oligonucleotide when the aptamer is in a state that it is not bound to a target substance but is not hybridizable when the aptamer is in a state that it is bound to the target substance. Described specifically, the three-dimensional structure of the aptamer changes between the state that it is bound to a target substance and the state that it is not bound to the target substance. As a result, the aptamer and the oligonucleotide hybridize with each other in the state that the aptamer is not bound to the target substance, but do not hybridize with each other in the state that the aptamer is bound to the target substance. The aptamer may preferably have such a structure that, even if the aptamer and the oligonucleotide hybridize with each other in advance, the coexistence of the target substance causes the aptamer to bind to the target substance and changes the structure of the aptamer, and as a result, the hybridized oligonucleotide separates.

Such a structure-switching aptamer, which can bind to a desired target substance, can be prepared, for example, by the known method described in Non-patent Document 2. According to this method, a single-stranded nucleic acid, which forms the single-stranded region and adjacent double-strand forming region, is synthesized first. This single-stranded nucleic acid is as described above, and as a preferred example, one having the base sequence represented by SEQ ID NO: 2 can be used. However, the single-stranded region is not limited to the above-exemplified base sequence but may have a desired base sequence. A region having a random base sequence is next added to the opposite ends of the thus-synthesized single-stranded nucleic acid. This addition can be easily conducted by successively binding nucleotides at random to the opposite ends of the single-stranded nucleic acid in an automated nucleic acid synthesizer. No particular limitation is imposed on the size of the region. In general, however, it may be 10 to 50-mers or so. Because the base sequence of this region is random, a nucleic acid library including huge kinds of nucleic acids is created. To the opposite ends of the nucleic acid, regions with which primers are to hybridize in PCR may next be added if desired. Insofar as the base sequences of these regions are known beforehand, no particular limitations are imposed at all on the sequences of the regions. No particular limitations are imposed on their sizes either. In general, however, their sizes may be 10-mers to 25-mers or so. It is to be noted that the addition of the regions, with which the primers are to hybridize, may be omitted because their addition correspondingly reduces the freedom of the sequence of the aptamer although their addition can obviate the need to determine the base sequence of the aptamer before the below-described PCR and can simplify the preparation steps of the aptamer.

On the side, the above-described immobilized oligonucleotide is provided. The nucleic acid library prepared as described above is next brought into contact with the immobilized oligonucleotide. This can be conducted, for example, by adding a solution of the nucleic acid library in a buffer to the immobilized oligonucleotide. As reaction conditions for the contact, it is simple and preferred to conduct the contact at room temperature because the adoption of the same conditions as those at the time of actual measurement of a target substance is preferred. It is possible to use, as the buffer, a buffer of a known composition similar to binding buffers employed in detection by known DNA probes. One example will also be described in the Examples to be described subsequently herein. No particular limitation is imposed on the reaction time. In general, however, the reaction time may be 1 minute to 30 minutes or so, preferably 10 minutes to 20 minutes. It is also preferred to set the number of molecules of the immobilized oligonucleotide greater than that of nucleic acids in the nucleic acid library. After the reaction, the solid phase is washed to eliminate the unbound nucleic acids. The nucleic acids included in the nucleic acid library all have the above-described single-stranded region, and on the other hand, the immobilized oligonucleotide hybridizes with the single-stranded region. Therefore, the nucleic acid molecules included in the nucleic acid library are all bound to the solid phase.

The target substance is next caused to act. As reaction conditions at this stage, it is also preferred to conduct the reaction at room temperature because the adoption of the same conditions as those at the time of actual measurement of the target substance is preferred. No particular limitation is imposed on the reaction time. In general, however, the reaction time may be 1 minute to 30 minutes or so, preferably 10 minutes to 20 minutes or so similar to the above-described reaction time. When the target substance is caused to act, the aptamer binds to the target substance. As a result of the binding to the target substance, the aptamer changes in structure, becomes no longer hybridizable with the immobilized oligonucleotide, and becomes liberated from the solid phase. On the other hand, neither the aptamer unbound to the target substance nor the aptamer capable of maintaining the hybridization with the immobilized oligonucleotide even after its binding to the target substance is liberated. Recovery of the aptamer liberated from the solid phase, therefore, makes it possible to collect only the aptamer which binds to the target substance and with the single-stranded region of which the oligonucleotide is hybridizable when the aptamer is in a state that it is not bound to the target substance but is not hybridizable when the aptamer is in a state that it is bound to the target substance. The recovery of the aptamer can be easily conducted by a usual method, that is, phenol extraction, ethanol precipitation or the like. The thus-collected aptamer is next amplified by PCR. When the regions with which primers are to hybridize in PCR were added upon preparation of the nucleic acid library, PCR is conducted using primers which hybridize with the regions. When the regions were not added, the base sequences of the respective collected aptamers are determined, and based on the base sequences, primers for PCR are chemically synthesized to conduct PCR. By conducting asymmetric PCR (one of the paired primers for use in PCR is used in an excess amount), the single-stranded nucleic acid can be amplified primarily. As an alternative, by using a biotinylated primer as one of primers for use in PCR, the amplified double-bonded nucleic acid is caused to bind to avidin beads. In this state, the nucleic acid is denatured, and the nucleic acid separated from the beads is then recovered to collect the single-stranded nucleic acid (the strand which is not biotinylated) from the amplified double-stranded nucleic acid.

The amplified aptamer is again brought into contact with the immobilized oligonucleotide, and the cycle consisting of the above-described steps is then repeated. By doing so, the aptamer hybridizes well with the immobilized oligonucleotide in the state that the aptamer is not bound to the target substance, but in the presence of the target substance, the aptamer binds well to the target substance and liberates well from the solid phase. As a greater fraction of the desired aptamer serves as a template for the PCR, progressive concentration of the desired aptamer is feasible. The principle of these steps is similar to SELEX invented for the first time as a preparation method of aptamers (Non-patent Document 1), and therefore, the above-described method can be considered to be a modification of SELEX.

The present inventors previously invented an improved method of SELEX, that allows an aptamer to evolve in silico (Non-patent Document 3). By applying the in silico evolution described in Non-patent Document 3 to the above-described method disclosed in Non-patent Document 2, the creation of a desired aptamer can be made efficient. According to this method, subsequent to the completion of the first cycle of the modified SELEX method, the base sequences of the resultant aptamers are determined, and further, their binding abilities to the target substance are measured and ranked. By the past research on aptamers, it is known that their basic structures are classified into four types, specifically the four types consisting of the hairpin type, the bulge type, the pseudoknot type and the guanine quartet type. A computer analysis makes it possible to readily ascertain which structure is taken by an aptamer of which base sequence and which nucleotide is needed for the retention of its basic structure. According to the method making use of the in silico evolution described in Non-patent Document 3, plural regions which are not indispensable for the retention of the basic structure of each aptamer and have, for example, 3 to 5-mers or so are shuffled at random between the corresponding regions in the resultant aptamers. Subsequently, random single-base substitutions are introduced into the respective regions after the shuffling. These shuffling and single-base substitutions are performed in silico. Aptamers which have been created in silico and have new base sequences are chemically synthesized to create a second nucleic acid library, which is then subjected to the above-described cycle. Upon preparation of the second nucleic acid library, the proportion of an aptamer having a region derived from an aptamer the binding ability of which was high in order is set at the largest, and the proportion of each remaining aptamer is decreased with the order. By artificially introducing mutations through in silico shuffling and single-base substitutions as described above, the efficiency of evolution by SELEX can be improved.

Figure 1:
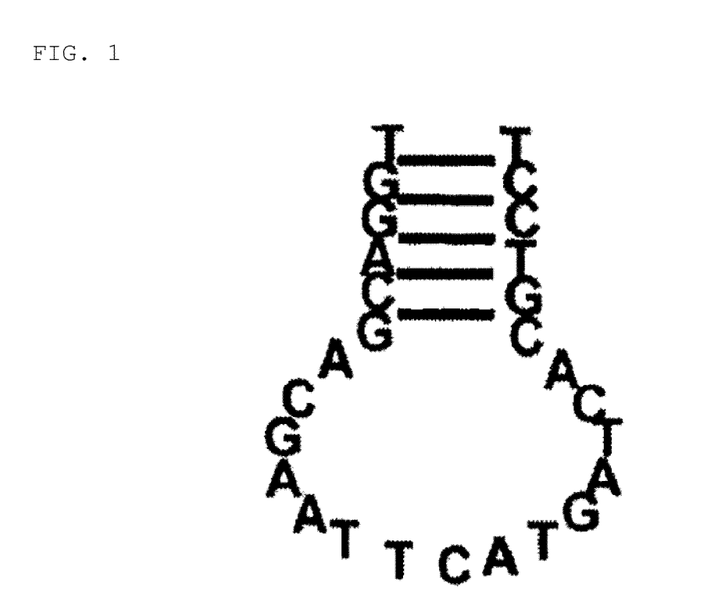
FIG. 1 A schematic illustration of a hairpin structure (SEQ ID NO: 7) including a looped, single-stranded region hybridizable with an immobilized oligonucleotide and contained in one specific example of the aptamer for use in the present invention.
Figure 2:
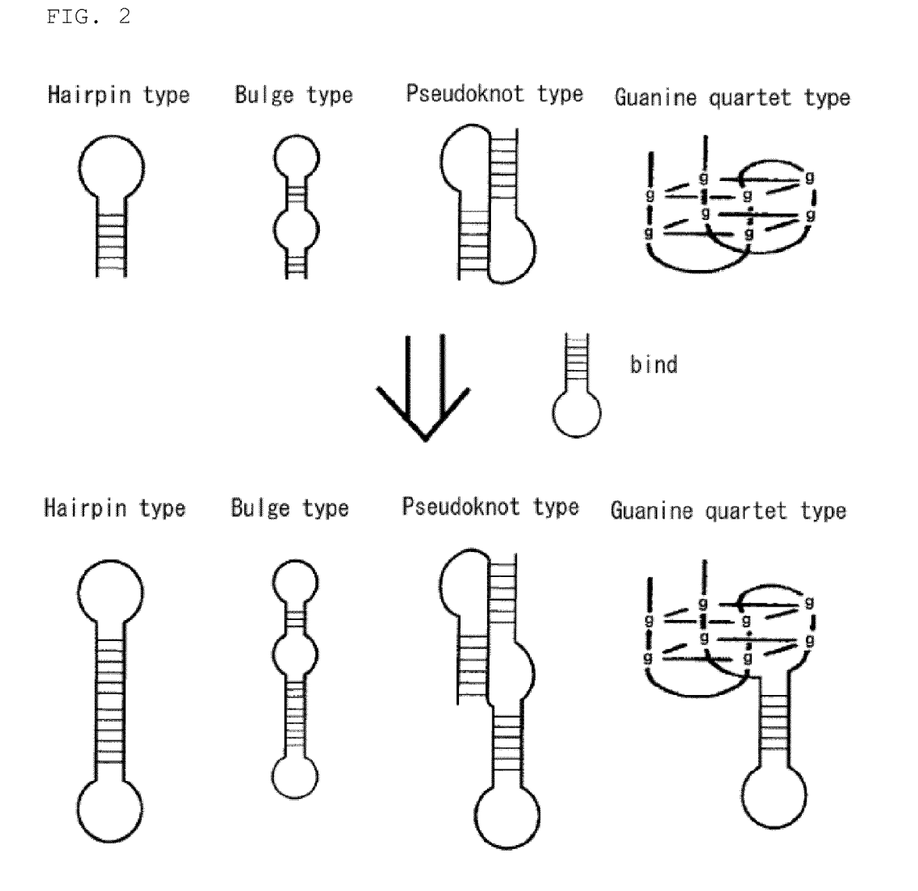
FIG. 2 A schematic illustration of positions at which the hairpin structure shown in FIG. 1 is inserted into aptamers having typical basic structures, respectively.

In the above-described method, the modified SELEX method is conducted using as a starting material a nucleic acid library that an absolutely random sequence is added to the opposite ends of a single-stranded region and adjacent double-strand forming region. When an aptamer that is to bind to a desired target substance is already known, the above-described structure-switching aptamer can be created based on the aptamer. This approach is considered to result in a higher efficiency in many instances. Described specifically, the basic structures of aptamers are known to be classified into the four types consisting of the hairpin type, the bulge type, the pseudoknot type and the guanine quartet type as described above. A single-stranded nucleic acid (SEQ ID NO: 7) obtained by binding a hairpin structure (SEQ ID NO: 2), which includes the above-described single-stranded region and adjacent double-strand forming region (a hairpin structure having the sequence represented by SEQ ID NO: 2 is shown by way of example in FIG. 1) to a region in a known aptamer, said region being considered to be irrelevant to the binding to the target substance, is highly likely to be a structure-switching aptamer useful in the present invention. Described specifically, those obtained by adding such a hairpin structure as that shown in FIG. 1 to aptamers of the respective types at the positions shown in FIG. 2 are highly likely to be desired structure-switching aptamers. A desired structure-switching aptamer is, therefore, obtainable with high possibility by preparing single-stranded nucleic acids having such structures and investigating their binding properties to the target substance and immobilized oligonucleotide. As an alternative, the above-described method can be made still more efficient by conducting the above-described modified SELEX method while using, as a nucleic acid library, single-stranded nucleic acids chemically synthesized beforehand by adding a hairpin structure to aptamers having a property of binding to the target substance. Even when an aptamer having desired structure-switching characteristics was not obtained by the addition of the hairpin structure shown in FIG. 2, the desired structure-switching aptamer can still be obtained by applying the method (Non-patent Document 3), which makes effective use of the above-described in silico evolution, to artificially create a mutation and conducting the above-described modified SELEX method while using it as a nucleic acid library. In this case, one or more nucleic acids each of which contains a mutation also introduced in the segment of the hairpin structure (including those modified in size) can also be included in a nucleic acid library. It is to be noted that the addition of the hairpin structure can also be conducted by progressively adding predetermined oligonucleotides to an original aptamer in an automated, chemical nucleic-acid synthesizer or by chemically synthesizing a single-chain nucleic acid, which contains the hairpin structure added thereto, from the beginning in an automated, chemical nucleic-acid synthesizer.

The technique that a hairpin structure is added to an aptamer as illustrated in FIG. 2 is particularly useful when an aptamer that is to bind to a desired target substance is already known. Even when an aptamer that is to bind to a desired target substance is unknown, the aptamer can also be prepared by forming an aptamer, which can bind to the desired target substance, by usual SELEX and adding a predetermined hairpin structure to it as described above. The present inventors invented an improved SELEX method capable of efficiently obtain an aptamer, which is higher in the binding ability to a target substance, in usual SELEX, and on the improved SELEX method, an application for patent has been filed (Japanese Patent Application 2005-200823). By creating an aptamer, which binds to a desired target substance, in accordance with the improved SELEX method and adding the hairpin structure to the aptamer as illustrated in FIG. 2, a structure-switching aptamer having excellent performance can be effectively obtained. Usual SELEX (Non-patent Document 1) includes bringing a nucleic acid library, which have random base sequences, into contact with a target substance immobilized on a carrier, collecting the nucleic acid bound to the target substance and determining its base sequence, amplifying the nucleic acid by PCR, and then repeating the above-described cycle while using the amplified nucleic acid as the nucleic acid library. The modified SELEX method described in Japanese Patent Application 2005-200823 includes allowing a carrier with a non-target substance immobilized thereon to coexist upon binding a desired target substance (the target substance in the present invention) and nucleic acids in a nucleic acid library to each other in usual SELEX, collecting only the nucleic acid that has bound to the desired target substance, amplifying the collected nucleic acid by PCR, collecting a single-stranded nucleic acid from the amplification mixture, bringing the single-stranded nucleic acid as a nucleic acid library into contact with a region where the target substance is immobilized, collecting the nucleic acid bound to the solid phase, amplifying the corrected nucleic acid to obtain a single strand, bringing the single strand again as a nucleic acid library into contact with the regions where the target substance and non-target substance are immobilized, respectively, and then repeating the cycle likewise. According to this method, the aptamers that bind to the non-target substance or the carrier are selected out, and the aptamer that specifically binds to the target substance is progressively concentrated. By adding a hairpin structure to the thus-obtained aptamer as described above, a desired structure-switching aptamer can be obtained.

When an aptamer that binds to a desired target substance is known, on the other hand, desired structure-switching properties may be obtained in some instances by making an appropriate selection as to the base sequence of an immobilized oligonucleotide (see Example 2 to be described subsequently herein). Described specifically, an aptamer known to bind to the desired target substance is employed as the aptamer thereby making an appropriate selection as to the base sequence of an immobilized oligonucleotide. As described above, an immobilized oligonucleotide generally has a base sequence that hybridizes at least partially to a single-stranded region of an aptamer. Nonetheless, appropriate selections are made as to the size and hybridizing region (which generally includes the single-stranded region of the aptamer at least partially as described above) of the immobilized oligonucleotide. In this case, it is preferred that the immobilized oligonucleotide has the base sequence complementary to the aptamer and at least a part of the base sequence is complementary to the single-stranded region of the aptamer. As the number of candidates for such an immobilized oligonucleotide is relatively small, such an immobilized oligonucleotide may often be obtained with relative ease by firstly conducting screening to collect immobilized oligonucleotides which bind to the desired target substance, and then screening them to collect an immobilized oligonucleotide which exhibits desired structure-switching properties.

Using the above-described immobilized oligonucleotide and labeled aptamer, the method of the present invention can be practiced as will be described next. Firstly, the target substance in a sample and the above-described labeled aptamer are brought into contact with each other. This can be achieved by mixing the sample and a solution of the labeled aptamer and incubating the resultant mixture. At this time, it is preferred to react the labeled aptamer in an excess amount relative to an assumed weight of the target substance in the sample and to make the entire target substance bind to the labeled aptamer. No particular limitation is imposed on the conditions for the incubation, but it is simple and preferred to conduct the incubation at room temperature. No particular limitation is imposed on the reaction time. In general, however, the reaction time is generally 1 minute to 30 minutes or so, preferably 10 minutes to 20 minutes or so.

The mixed solution of the sample and the labeled aptamer is next brought into contact with the above-described immobilized oligonucleotide. This can be achieved by mixing a carrier, on which the above-described oligonucleotide is immobilized, with the mixed solution of the sample and the labeled aptamer. When the carrier on which the oligonucleotide is immobilized is in the form of a column or filter, it is only necessary to simply pass the mixed solution through the column or filter. The amount of the immobilized oligonucleotide is set greater than the mixed labeled aptamer such that, even when the target substance does not exist in the sample, the added, unreacted, labeled aptamer hybridizes in its entirety to the immobilized oligonucleotide. As conditions for the incubation, it is simple and preferred to conduct the incubation at room temperature as in the conditions adopted in the modified SELEX upon creation of the aptamer. No particular limitation is imposed on the reaction time. In general, however, it may be 1 minute to 30 minutes or so, with 10 minutes to 20 minutes or so being preferred.

When the target substance is contained in a sample, the target substance binds to the labeled aptamer. The labeled aptamer with the target substance bound thereto cannot hybridize with the immobilized oligonucleotide as described above. On the other hand, the labeled aptamer which has not bound to the target substance hybridizes with the immobilized oligonucleotide so that it is bound on the solid phase and does not exist in a free state.

In the next step, the label of the labeled aptamer which has not bound to the solid phase is measured. Because the labeled aptamer which has not bound to the solid phase is the aptamer bound to the target substance as described above, the target substance in the sample can be measured by measuring the label of the labeled aptamer which has not bound to the solid phase. The solid phase and the solution after its incubation together with the solid phase can be easily separated from each other. When the solid phase includes beads, for example, the solution after the incubation can be collected by recovering a supernatant through centrifugal separation. When a column-shaped carrier or filter-shaped carrier is adopted as the solid phase, a solution with the free labeled aptamer contained therein can be collected by recovering a solution which has passed through the column or filter. As the label itself, it is possible to use one commonly used in immunoassay as described above. Accordingly, the measurement of the label can be performed depending on the label by a usual method commonly employed in the field of immunoassay. When the label is a fluorescent label, for example, the fluorescence intensity of the collected solution is measured. When the label is an enzyme, a substrate required for an enzyme reaction is added and the product occurred by the enzyme reaction is measured. In the case of an enzyme that catalyzes an electrochemical reaction, a working electrode, an opposing electrode and a reference electrode are immersed in a solution in which a substrate for the enzyme has been added, and an electromotive force occurred between the working electrode and the opposing electrode is measured. The measurement is the same as the measurement of an enzyme reaction by the use of a conventional enzyme electrode, and can be readily performed by a usual method.

In the above-described method, the sample and the labeled aptamer were mixed first, and the resulting mixed solution was then reacted with the immobilized oligonucleotide. However, in the case of an aptamer which can be created by the above-described method and cannot hybridize with an oligonucleotide in the presence of the target substance, it is not absolutely necessary to react the sample with the labeled aptamer first. The three of the sample, labeled aptamer and immobilized oligonucleotide may be reacted simultaneously, or the sample and the immobilized oligonucleotide can be reacted first, followed by the reaction of the labeled aptamer.

In the method of the present invention, the separation of the aptamer bound to the target substance and the aptamer failed to bind to the target substance from each other, in other words, the so-called B/F separation can be conducted by separation between the solid phase and the solution. Therefore, the separation is extremely simple and can be practiced without needing any special equipment. Needless to day, it is possible to design an apparatus capable of easily practicing the method of the present invention, for example, by simply dropping a sample solution. In essence, such an apparatus is equipped at least with a solid phase, on which an oligonucleotide is immobilized, and a capture region where the aptamer is captured after its contact with the solid phase. In such an apparatus, the measurement system can be simplified, and the adoption of electrochemical measurement which facilitates miniaturization, integration and mass production is preferred. Described specifically, an enzyme that catalyzes an electrochemically-measurable reaction can be adopted as the label of the aptamer, and electrodes or a region which are in direct contact with electrodes can be preferably adopted as the capture region.

As such a measurement system, a system employed in immunochromatography for immunoassay can be applied. One of the present joint applicants previously invented a biosensor for immunoassay, which can electrochemically measure a label enzyme with ease (Patent Documents 1 to 3). By applying the principle of such a biosensor, a measurement system capable of easily practicing the method of the present invention can be designed. Described specifically, a measurement system can be constructed, for example, by placing an electrode plate (working electrode and opposing electrode) on a substrate; stacking on the electrode plate an electrochemical reaction layer with a substrate contained therein for a label enzyme; stacking on the electrochemical reaction layer a layer with an oligonucleotide immobilized therein; and then stacking on the oligonucleotide layer a layer with a labeled aptamer contained therein. Here, each layer is formed of a porous layer through which a liquid can pass, such as a membrane or filter. The labeled aptamer is such one that can be readily separated from the associated porous layer by the addition of the liquid like one impregnated in the porous layer. Similarly, the substrate contained in the electrochemical reaction layer may preferably be held such that it can be readily separated from the associated layer by the liquid.

When the sample solution is dropped into the labeled aptamer layer in such an apparatus, the sample solution comes into contact with the labeled aptamer in the labeled aptamer layer so that the target substance and the labeled aptamer bind to each other. The labeled aptamer bound to the target substance and the labeled aptamer failed to bind to the target substance are both eluted into the immobilized oligonucleotide layer disposed below the labeled aptamer layer. In the immobilized oligonucleotide layer, only the labeled aptamer failed to bind to the target substance hybridizes with the oligonucleotide and is trapped on the solid phase, and the labeled aptamer bound to the target substance advances into the electrochemical reaction layer disposed below the immobilized oligonucleotide layer. In this apparatus, the electrochemical reaction layer serves as a capture region that captures the aptamer subsequent to its contact with the immobilized oligonucleotide. As the substrate for the labeled enzyme is contained in the electrochemical reaction layer, the labeled enzyme reacts to the substrate there so that an electromotive force occurs between the electrodes. By measuring this electromotive force, the target substance in the sample can be measured. As has been described above, the use of the above-described measurement system makes it possible to measure the target substance in the sample solution only by simply dropping the sample solution into the system and measuring a voltage across the electrodes, and therefore, the measurement system is extremely convenient.

The above-described apparatus is of the type that a sample solution is allowed to flow by gravity from the top to the bottom, in other words, is a flow-through type apparatus. It can be constructed as a lateral-flow type apparatus which is also commonly employed in addition to the flow-through type in immunoassay. A lateral-flow type apparatus causes a liquid to move in a horizontal direction by using capillary action, and its principle is similar to that of the flow-through type apparatus. Described specifically, a labeled aptamer region with a labeled aptamer contained therein is disposed at an end portion of a single porous layer; next to the labeled aptamer region, an immobilized oligonucleotide region in which the oligonucleotide is immobilized; next to the immobilized oligonucleotide region, an electrochemical reaction region with a substrate for a label enzyme is disposed; and next to the electrochemical reaction region, a working electrode and an opposing electrode are disposed in contact with the electrochemical reaction region. Its operation principle is similar to the principle in the case of the flow-through type. Described specifically, when the sample solution is dropped into the labeled aptamer layer at an end of the apparatus, the target substance and the labeled aptamer bind to each other, the bound labeled aptamer and the unreacted labeled aptamer are caused to flow by capillary action into the subsequent oligonucleotide immobilization region, the labeled aptamer failed to bind to the target substance is trapped there, only the labeled aptamer bound to the target substance is caused to flow into the subsequent electrochemical reaction region and reacts to the substrate there to undergo an electrochemical reaction, and its electromotive force is then measured via the electrodes arranged in contact with the region. It is to be noted that—when with the sample solution alone, there is no liquid amount sufficient to allow the labeled aptamer to flow into the electrochemical reaction region by capillary action—a developer may be added further to the labeled aptamer region.

The present invention will hereinafter be described specifically based on Examples. It is, however, to be noted that the present invention shall not be limited to the following Examples.

Example 1

1. Preparation of Thrombin-Binding Aptamer

Figure 3:
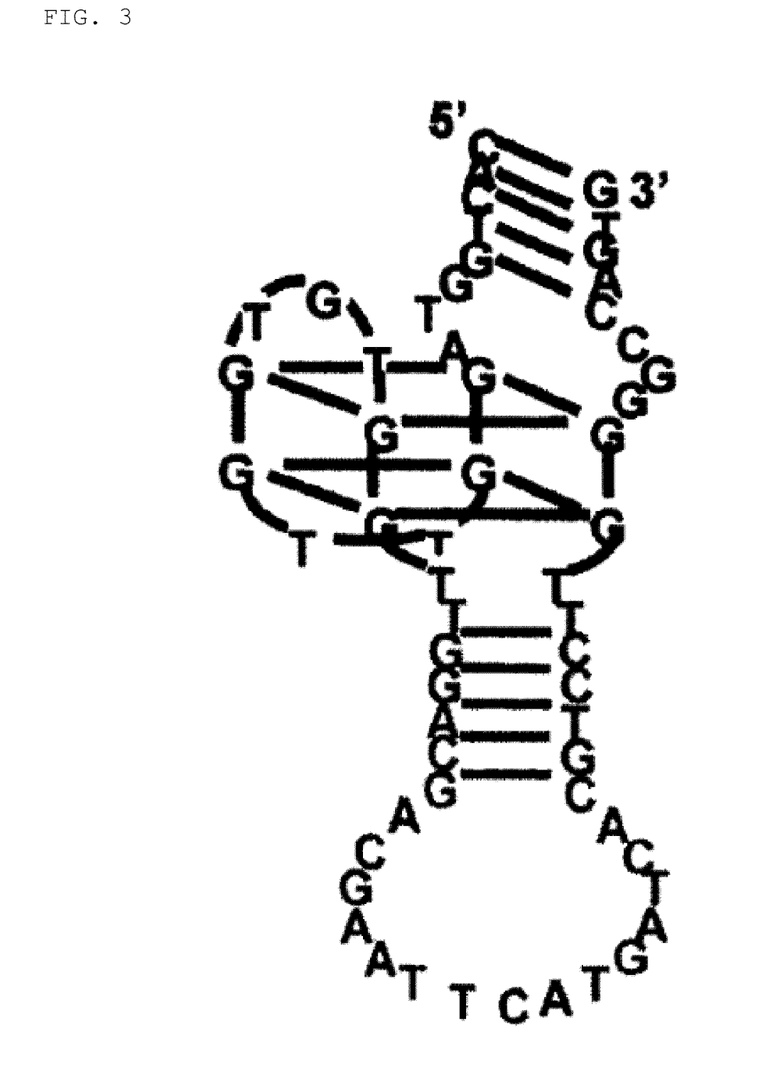
FIG. 3 A schematic illustration of a three-dimensional structure of an aptamer (SEQ ID NO: 4) prepared in Example 1 of the present invention.

The aptamer (SEQ ID NO: 3) which is known to specifically bind to thrombin is an aptamer having the guanine quartet structure. A structure-switching aptamer was prepared by inserting the hairpin structure of SEQ ID NO: 2 into the aptamer of SEQ ID NO: 3. In particular, single-stranded DNA having the base sequence represented by SEQ ID NO: 4 was chemically synthesized with a hairpin structure, (the base sequence represented by SEQ ID NO: 2) being connected between the t and t in the loop composed of the t and t that mutually connect the guanines which forms the second guanine quartet as counted from the end of the guanine quartet structure of SEQ ID NO: 3. In the base sequence represented by SEQ ID NO: 4, 22 nt (the 22nd nucleotide from the 5'-end; the same shall apply hereinafter) to 46 nt correspond to the hairpin structure inserted to obtain the aptamer for use in the present invention, the 15-mers of from 27 nt to 41 nt is the single-stranded region that forms the loop in the hairpin structure, 22 nt to 26 nt and 42 nt to 46 nt correspond to the adjacent double-strand forming region, and 22 nt and 46 nt, 23 nt and 45 nt, 24 nt and 44 nt, 25 nt and 43 nt, and 26 nt and 42 nt are paired, respectively, to form the double-stranded region of 5-mers. The three-dimensional structure of this aptamer (SEQ ID NO: 4) is schematically illustrated in FIG. 3.

2. Confirmation of Structure-Switching Properties

As will be described below, the aptamer (SEQ ID NO: 4) prepared above in Procedure 1 was confirmed to have structure-switching properties that it binds to thrombin and that in the absence of thrombin, it hybridizes with an oligonucleotide as a complementary strand (15-mers; having SEQ ID NO: 8) to the 27 nt to 41 nt in SEQ ID NO: 4 (hereinafter called "15-mer complementary strand" for the sake of convenience) but under the coexistence of thrombin and the 15-mer complementary strand, it binds to thrombin and fails to bind to the 15-mer complementary strand. The aptamer (6 μM) and thrombin (54 nM) were mixed in a detection buffer (10 mM MOPS buffer (pH 7.4)). Subsequent to incubation at room temperature for 15 minutes, the 15-mer complementary strand which had been modified with FITC (6 μM) was added, followed by further incubation at room temperature for 15 minutes. The incubation mixture was subjected to electrophoresis with 15% polyacrylamide gel. For the sake of comparison, similar electrophoresis was also conducted with respect to the FITC-modified 15-mer complementary strand alone and also with respect to a mixture of the FITC-modified 15-mer complementary strand and the aptamer. Further, using the aptamer (4 μM), thrombin (0.5 to 4 μM) and the FITC-modified 15-mer complementary strand (4 μM), electrophoresis was also performed likewise. After a band of the FITC-modified 15-mer complementary strand was confirmed by an image analyzer ("TYPHOON," trade name; manufactured by Amersham Bioscience) subsequent to each electrophoresis, a band of DNA was detected by ethidium bromide.

As a result of the electrophoresis experiment at each fixed thrombin concentration, the electrophoresis band shifted toward the high-molecular side in the case of the mixture of the FITC-labeled 15-mer complementary strand and the aptamer than in the case of the FITC-labeled 15-mer complementary strand alone. From this, the aptamer was confirmed to hybridize with the FITC-labeled 15-mers. With a mixture obtained by successively incubating the three of the aptamer, FITC-labeled 15-mer complementary strand and thrombin, on the other hand, the band of the FITC-labeled 15-mer complementary strand did not shift and was formed at a position corresponding to the aptamer-thrombin complex. With an aptamer-thrombin complex formed beforehand, the FITC-labeled 15-mer complementary strand was not confirmed to hybridize with the aptamer even when the FITC-labeled 15-mer complementary strand was caused to coexist subsequently. As a result of the electrophoresis experiment at the varied thrombin concentrations, as the amount of thrombin became smaller, the band indicating the hybridization between the aptamer while the FITC-labeled 15-mer complementary strand became denser and the band indicating the single strand of the 15-mer complementary strand became thinner. This indicated that the hybridization between the 15-mer complementary strand and the aptamer took place at a higher rate as the concentration of thrombin became lower. It was, therefore, confirmed that the free aptamer failed to recognize thrombin underwent hybridization with the 15-mer complementary strand.

3. Measurement of Thrombin Concentration in Sample

Because the aptamer prepared above in Procedure 1 was confirmed above in Procedure 2 to have the desired structure-switching properties that it binds to thrombin that it binds to the 15-mer complementary strand in a state that it is not bound to thrombin but it does not bind to the 15-mer complementary strand in a state that it is bound to thrombin, the 15-mers were bound to a carrier to quantitate thrombin in a sample. This operation was conducted as will be described hereinafter.

(1) Preparation of DNA-Immobilized Carrier

To "NEUTRAVIDIN Beads" (trade name, product of Thermo Scientific Pierce Protein Research Products; deglycosylated avidin bound on agarose beads; 10 μL), a biotin-modified 15-mer complementary strand (0.5 nmol) was added. With a binding buffer (100 mM phosphoric acid, 150 mM NaCl (pH 7.2)), the total volume was adjusted to 500 µL. The resultant mixture was stirred at room temperature for 1 hour to immobilize the 15-mer complementary DNA strand on the avidin beads. It is to be noted that the 15-mer complementary was biotinylated at its 5'-end upon its synthesis. Subsequently, the avidin beads were collected by centrifugal separation, blocked and washed with 4 mM biotin for 15 minutes and then with 1% blocking buffer (hybridization grade, product of Roche Diagnostics) for 30 minutes, and then provided as a DNA-immobilized carrier.

(2) Labeling of Aptamer

The aptamer prepared above in Procedure 1 was labeled with pyrroloquinoline quinone glucose dehydrogenase (hereinafter, "PQQGDH") by the glutaraldehyde crosslinking method. Specifically, the labeling was conducted as will be described next. PQQGDH, which had been activated in the presence of 1 mM $CaCl_2$ and 1 µM PQQ (pyrroloquinoline quinone), and avidin were mixed in amounts of 0.48 mg and 0.52 mg, respectively, in 10 mM MOPS buffer. Subsequently, glutaraldehyde was added to give a final concentration of 0.1%, followed by stirring at room temperature for 30 minutes. To suspend the reaction, the resulting mixture was dialyzed for 1 to 3 hours against 10 mM Tris-HCL buffer (pH 7.5), and then for 6 hours or longer against 10 mM MOPS buffer. It is to be noted that PQQGDH is an enzyme, which uses glucose as a substrate and catalyzes a reaction that dehydrogenates glucose, and can electrochemically measure the concentration of glucose.

(3) Measurement of Thrombin Concentration

Each sample solution (100 µL), which contained thrombin (0 to 10 µg/mL, 0 to 27 µM) and the PQQGDH-labeled aptamer (0.1 U, approx. 10 µmol) prepared above in Procedure (2), was added to the DNA-immobilized carrier (10 µL) obtained above in Procedure (1), and the resulting mixture was stirred at room temperature for 15 minutes and then centrifuged. Using the thus-obtained supernatant (20 µL) and 10 mM MOPS (pH 7.2, 4 mL in total), which contained mPMS (1-methoxyphenazine methosulphate) (6 mM), PQQ (1 µM) and $CaCl_2$ (1 mM), as a reaction solution, a gold electrode as a working electrode and a platinum electrode as an opposing electrode, the response current was measured at an impression potential of +100 mV vs Ag/AgCl while adding glucose to a final concentration of 60 mM. The measurement was conducted at 25° C. With respect to each of sample solutions containing thrombin at 50 to 1,000 µg/mL (54 to 2,700 µM), detection was similarly conduced by doubling the amounts of the DNA-immobilized carrier and ap-GDH to be employed.

Figure 4:
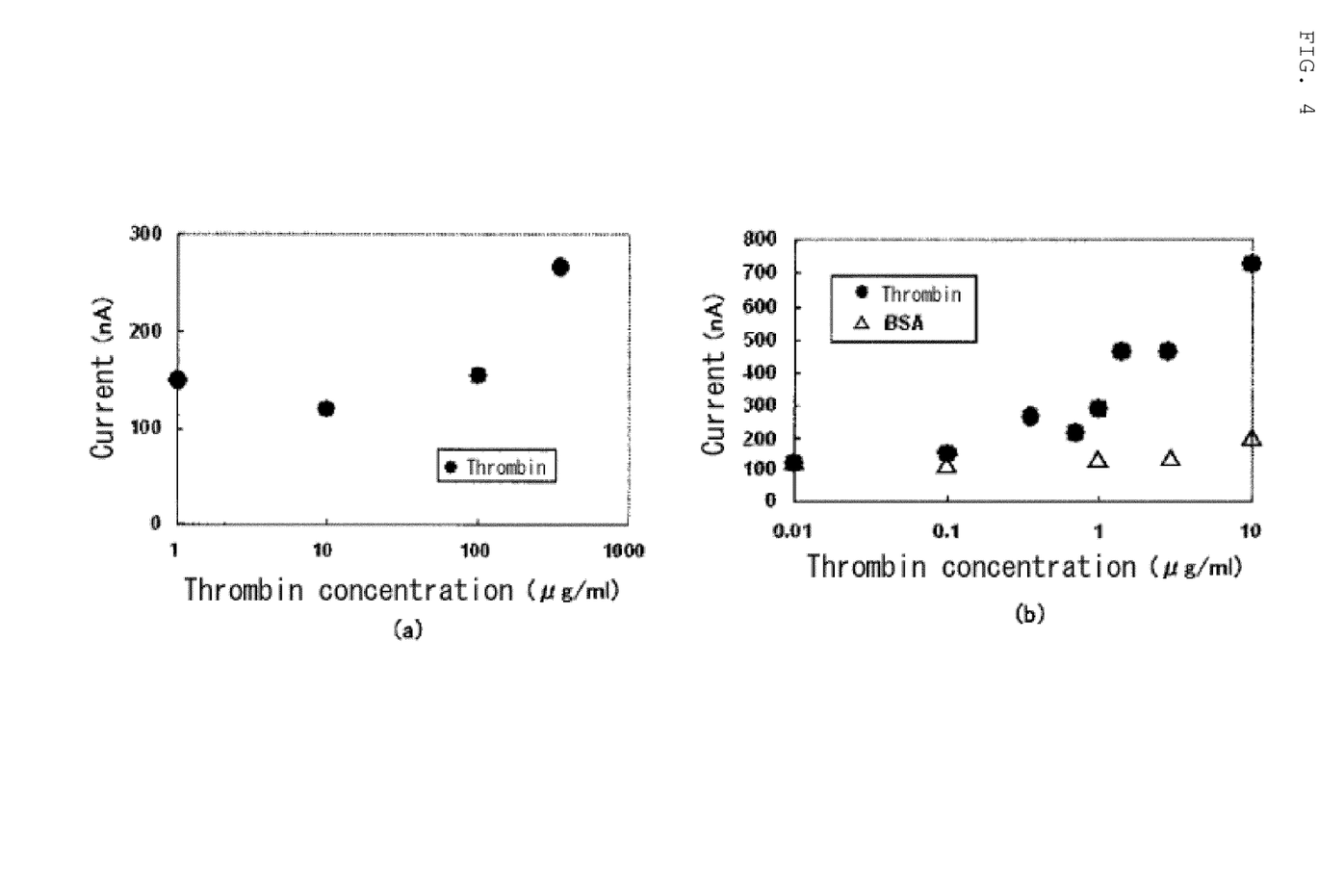
FIG. 4 A schematic diagram of a correlation between the concentrations of thrombin in samples and detected current values as measured in Example 1 of the present invention.
Figure 5:
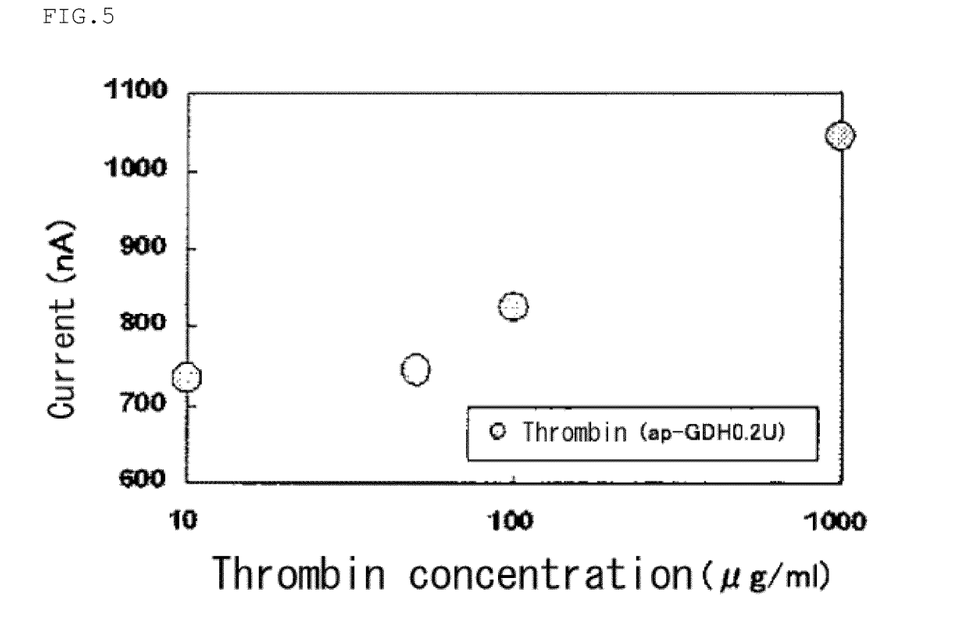
FIG. 5 A diagram illustrating the results of measurement of thrombin concentrations in a concentration range higher than that shown in FIG. 4.

The results are shown in FIG. 4 and FIG. 5. A thrombin-concentration-dependent increase in current value was observed up to the level of 10 µg/mL. When BSA was used as a control in place of thrombin, the resultant current value was low, no BSA-concentration-dependent increase in current value was observed (FIG. 4(*b*)), and the detection limit was 100 ng/mL (2.7 nM) (FIG. 4(*a*)). At thrombin concentrations of 10 µg/mL and higher, a thrombin concentration-dependent increase in current value was observed to the level of 1 mg/mL (27 mM) by doubling the amounts of the immobilizing carrier and ap-GDH to be used (FIG. 5). When thrombin abundantly exists in a sample solution, ap-GDH is bound to the thrombin in the sample solution and remains in the supernatant without hybridization with the 15-mer complementary strand on the immobilizing carrier. As a consequence, a high response current is considered to have been exhibited upon addition of glucose. It has, therefore, been demonstrated that thrombin can be detected based on this principle.

Example 2

1. IgE-Binding Aptamer

Figure 6:
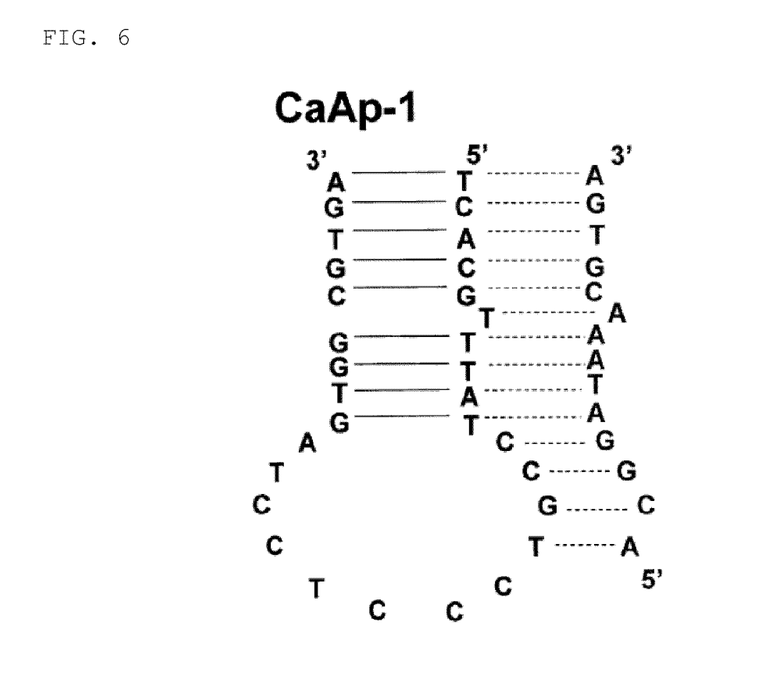
FIG. 6 An illustration of the base sequence and secondary structure of an IgE-binding aptamer (SEQ ID NO: 5) and the base sequence and hybridization positions of an immobilized oligonucleotide (SEQ ID NO: 6), both employed in Example 2 of the present invention.

Employed as an IgE-binding aptamer was the aptamer known to bind to IgE (Non-patent Document 4) (hereinafter, "CaAp-1"). The base sequence of this CaAp-1 is represented by SEQ ID NO: 5, and its base sequence and two-dimensional structure are shown in FIG. 6. As shown in FIG. 6, CaAp-1 is composed of a single hairpin structure having a single-stranded region. It is to be noted that CaAp-1 was chemically synthesized by an automatic nucleic acid synthesizer.

2. Confirmation of Binding Property with IgE by SPR

Biotinylated CaAp-1 was immobilized on an SPR chip (SA chip), and variations in SPR signal when IgE solutions of various concentrations (100 µL) were fed were observed. Upon measurement of interaction, an Mg2+-containing PBS buffer (138 mM NaCl, 2.7 mM KCl, 8.1 mM $NaHPO_4$, 1.1 mM $KHPO_4$, 1 mM $MgCl_2$, pH 7.4) was used, and the flow rate was set at 20 µL/min. Observed as a control were variations in SPR signal when bovine serum albumin (BSA) solutions of various concentrations were fed.

As a result, no variations in signal were observed when BSA was fed. When IgE was fed, however, the signal varied depending on its concentration. From the foregoing, CaAp-1 was confirmed to specifically bind to IgE as described in Non-patent Document 4.

3. Selection of Immobilized Oligonucleotide

Oligonucleotides complementary to the 8-mer, 10-mer and 12-mer regions from the 5'-end of CaAp-1 (SEQ ID NO: 5) were prepared, and similar to the case of the below-described 14-mer oligonucleotide, were incubated together with CaAp-1 and then subjected to electrophoresis to investigate their binding property to CaAp-1 (whether or not they would hybridize). As a result, none of the oligonucleotides hybridized with CaAp-1 at room temperature.

Therefore, an oligonucleotide complementary to the 14-mer region from the 5-end of CaAp-1 (hereinafter called "the 14-mer capture oligonucleotide"; having SEQ ID NO: 6) was prepared, and its binding property with CaAp-1 was investigated by electrophoresis. Described specifically, after 1 µM aptamer and 0 to 1 µM IgE were mixed together in PBS (pH 7.0) and were then incubated at room temperature for 15 minutes, the FITC-modified 14-mer capture oligonucleotide (1 µM) was added, followed by further incubation at room temperature for 15 minutes. The incubation mixture was then subjected to electrophoresis with 15% polyacrylamide gel. Subsequent to the electrophoresis, a band of the FITC-modified 15-mer capture oligonucleotide was confirmed by the image analyzer ("TYPHOON," trade name).

As a result, the 14-mer capture oligonucleotide (SEQ ID NO: 6) hybridized with CaAp-1 (SEQ ID NO: 5) under the above-described conditions in the absence of IgE, and in the presence of IgE, as the concentration of IgE increased, the amount of the CaAp-1-binding, 14-mer capture oligonucleotide decreased and the amount of the IgE-binding 14-mer capture oligonucleotide increased. As a result, CaAp-1 has been confirmed to have the desired structure-switching properties that in the absence of the target substance (IgE), it binds to the 14-mer capture oligonucleotide but in the presence of the target substance, it binds to the target substance without binding to the 14-mer capture oligonucleotide.

FIG. 6 illustrates the base sequence (SEQ ID NO: 6) of the 14-mer capture oligonucleotide and the manner of its hybridization with CaAp-1 (SEQ ID NO: 5). As is evident from FIG. 6, the 14-mer capture oligonucleotide hybridizes at 4-mers (about 29% of 14-mers) thereof with the single-strand region of CaAp-1.

4. Electrochemical Detection of IgE by Use of 14-mer Capture Oligonucleotide Immobilized Beads To beads (20 µL; solid amount: 10 µL) with "NEUTRA-VIDIN" (trade name) immobilized as a biotin-binding substance thereon, the biotin-modified 14-mer capture oligonucleotide (0.5 nmol) was added. With 100 mM phosphate buffer and 150 mM NaCl2 (pH7.2), the total volume was adjusted to 500 µL. The resultant mixture was stirred overnight at 4° C. to immobilize the 14-mer capture oligonucleotide on the beads. Subsequently, the beads were blocked and washed with 4 mM biotin for 15 minutes and then with 1% blocking buffer for 1 hour, and were then provided as a DNA-immobilized carrier. IgE (0 to 1 µM) and the PQQGDH-labeled CaAp-1 (0.1 U; prepared by the GA crosslinking method, approx. 10 pmol) were mixed together. The total volume of the resulting mixture was adjusted to 100 µL, followed by incubation at room temperature for 15 minutes. The thus-prepared sampled solution was added to the DNA-immobilized beads, the resulting mixture was stirred for 15 minutes at room temperature, and by centrifugation, the supernatant was collected. Using the supernatant (20 µL) and 10 mM MOPS (pH 7.2), which contained CaCl2 (1 mM) and PQQ (1 µM), as a reaction solution (total volume: 4 mL), a gold electrode as a working electrode and a platinum electrode as an opposing electrode, the response current was measured at an impression potential of +100 mV vs Ag/AgCl while adding glucose to a final concentration of 60 mM. As a control, a similar operation was conducted using BSA in place of IgE.

Figure 7:
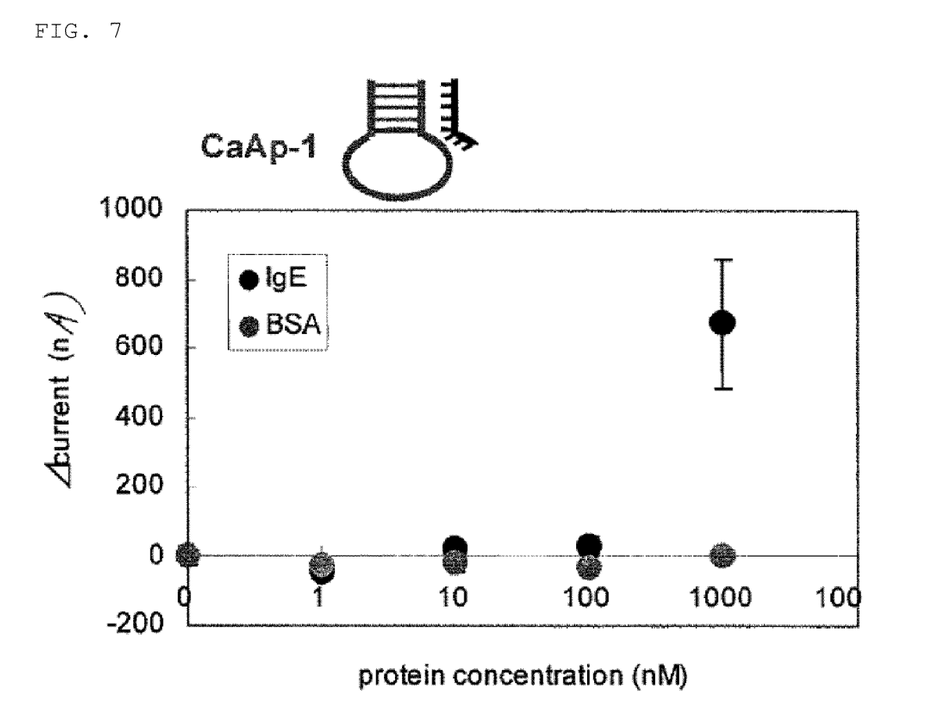
FIG. 7 A diagram of a correlation between the concentrations of IgE in samples and detected current values as measured in Example 2 of the present invention.

The results are shown in FIG. 7. As is indicated in FIG. 7, a response current was detected when IgE was at 1,000 nm (1 µM). With BSA at the same concentration, on the other hand, no response current was detected. It has been found from the foregoing that IgE can be measured by the method of the present invention which uses CaAp-1 as an aptamer and the 14-mer capture oligonucleotide as an immobilized oligonucleotide.

The invention claimed is:

1. A method for assaying a target substance in a sample, comprising:
    simultaneously or successively bringing into contact together:
        (A) a labeled aptamer, which has a property of binding to said target substance and is hybridizable to an oligonucleotide when said labeled aptamer is not bound to said target substance, but is not hybridizable to said oligonucleotide when said labeled aptamer is bound to said target substance,
        (B) said target substance in said sample, and
        (C) a solid phase substrate or carrier, on which said oligonucleotide has been immobilized in an excess amount relative to said target substance; and
    measuring the label of said aptamer which has not been bound on said solid phase, wherein the measurement of the label of said aptamer provides an assay of the target substance in said sample.

2. The method according to claim 1, wherein said aptamer has a looped, single-stranded region, and wherein regions on adjacent opposite ends of said single-stranded region are hybridizable to one another to form a double-stranded region.

3. The method according to claim 2, wherein said single-stranded region has a length of from 8 to 25 nucleotides.

4. The method according to claim 2, wherein said double-stranded region has a length of from 2 to 10 base pairs.

5. The method according to claim 2, wherein said oligonucleotide comprises a region which is complementary to at least a continuous part of said single-stranded region and which has a length of from 4 to 25 nucleotides.

6. The method according to claim 5, wherein said oligonucleotide comprises a region which is complementary to at least a continuous part of said single-stranded region and which has a length of from 8 to 25 nucleotides.

7. The method according to claim 6, wherein said oligonucleotide comprises a region which is complementary to said single-stranded region and has the same length as said single-stranded region.

8. The method according to claim 3, wherein said single-stranded region has a base sequence of acgaattcatgatca (SEQ ID NO:1).

9. The method according to claim 8, wherein said single-stranded region and regions adjacent opposite ends of said single-stranded region have a base sequence of ggacgacgaat-tcatgatcacgtcc (SEQ ID NO:2).

10. The method according to claim 1, wherein after said aptamer and said target substance are mixed, the resulting mixture is brought into contact with said solid phase, and in said mixture, said aptamer is contained in an excess amount relative to said target substance.

11. The method according to claim 1, wherein said label is an enzyme.

12. The method according to claim 11, wherein said enzyme is an enzyme that catalyzes an electrochemically-measurable reaction, and said enzyme bound to said aptamer which has not bound to said solid phase is electrochemically measured.

13. The method according to claim 12, wherein said enzyme is glucose dehydrogenase.

14. The method according to claim 1, wherein said solid phase substrate or carrier is a solid phase carrier.

15. The method according to claim 1, wherein said target substance is a protein.

16. The method according to claim 15, wherein said target substance is a hormone.

17. The method according to claim 15, wherein said target substance is a cancer-associated antigen.

18. The method according to claim 15, wherein said target substance is an antibody that specifically binds a virus.

19. The method according to claim 1, further comprising:
separating the aptamer which has not been bound on said solid phase from the solid phase prior to said measuring the label of said aptamer which has not been bound on said solid phase.

* * * * *